US010258518B2

(12) United States Patent
Carlén et al.

(10) Patent No.: US 10,258,518 B2
(45) Date of Patent: Apr. 16, 2019

(54) PACK MODULE COMPRISING ABSORBENT ARTICLES AND AT LEAST ONE BELT FUNCTIONING AS GRIPPING DEVICE

(75) Inventors: Henrik Carlén, Västra Frölunda (SE); Roy Hansson, Mölndal (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 168 days.

(21) Appl. No.: 14/233,676

(22) PCT Filed: Jun. 29, 2012

(86) PCT No.: PCT/SE2012/050739
§ 371 (c)(1),
(2), (4) Date: Jan. 17, 2014

(87) PCT Pub. No.: WO2013/012374
PCT Pub. Date: Jan. 24, 2013

(65) Prior Publication Data
US 2014/0202907 A1 Jul. 24, 2014

(30) Foreign Application Priority Data
Jul. 18, 2011 (CN) .......................... 2011 1 0213021

(51) Int. Cl.
*A61F 13/64* (2006.01)
*A61F 13/551* (2006.01)
(Continued)

(52) U.S. Cl.
CPC .. *A61F 13/55105* (2013.01); *A61F 13/55115* (2013.01); *A61F 13/55145* (2013.01);
(Continued)

(58) Field of Classification Search
CPC ................ B65D 85/16; B65D 83/0805; A61F 13/49004; A61F 13/55105; A61F 13/55115; A61F 13/64; A61F 13/66
(Continued)

(56) References Cited

U.S. PATENT DOCUMENTS 2,258,170 A * 10/1941 Austin et al. .................. 221/259
2,415,117 A * 2/1947 Tamarin .......................... 221/32
(Continued)

FOREIGN PATENT DOCUMENTS

CN 1902105 A 1/2007
CN 1997572 A 7/2007
(Continued)

OTHER PUBLICATIONS

International Search Report (PCT/ISA/210) dated Oct. 15, 2012, by the Swedish Patent Office as the International Searching Authority for International Application No. PCT/SE2012/050739.
(Continued)

*Primary Examiner* — J. Gregory Pickett
*Assistant Examiner* — Jenine Pagan
(74) *Attorney, Agent, or Firm* — Buchanan Ingersoll & Rooney PC (57) ABSTRACT

A pack module includes a number of absorbent articles and at least one belt to which the absorbent articles can be releasably attached. The belt when placed in the pack module constitutes a gripping device which is intended to act on at least one of the articles and, at least partially, remove at least one absorbent article from the pack module when the gripping device is used. Removal of firmly compressed absorbent articles from a pack module without using additional material in the pack module is thus possible.

15 Claims, 6 Drawing Sheets

(51) Int. Cl.
  *B65D 75/58*   (2006.01)
  *B65D 85/07*   (2017.01)
  *B65D 83/08*   (2006.01)
(52) U.S. Cl.
  CPC .......... *A61F 13/64* (2013.01); *B65D 75/5827* (2013.01); *B65D 83/0811* (2013.01); *B65D 85/07* (2018.01)
(58) Field of Classification Search
  USPC ........ 206/494, 438, 440, 812, 804; 604/391, 604/392
  See application file for complete search history.

(56) References Cited

U.S. PATENT DOCUMENTS

| | | | |
|---|---|---|---|
| 2,812,057 A * | 11/1957 | Brownfield | 206/250 |
| 3,923,239 A * | 12/1975 | Lee | 206/250 |
| 4,934,535 A | 6/1990 | Muckenfuhs et al. | |
| 5,377,837 A | 1/1995 | Roussel | |
| 5,380,094 A | 1/1995 | Schmidt et al. | |
| H1440 H * | 5/1995 | New | A61F 5/4401 604/385.21 |
| 5,662,636 A * | 9/1997 | Benjamin | A61F 13/494 604/385.28 |
| 5,906,604 A | 5/1999 | Rönnberg et al. | |
| 5,971,970 A | 10/1999 | Carlbark et al. | |
| 6,334,858 B1 * | 1/2002 | Ronnberg et al. | 604/392 |
| 6,342,050 B1 | 1/2002 | Rönnberg et al. | |
| 7,708,729 B2 | 5/2010 | Rönnberg et al. | |
| 7,850,673 B1 | 12/2010 | Carlbark et al. | |
| 2005/0155888 A1 | 7/2005 | Osterdahl et al. | |
| 2005/0256494 A1 * | 11/2005 | Datta | A61F 13/15747 604/385.201 |
| 2007/0175789 A1 | 8/2007 | Ronnberg et al. | |
| 2008/0004590 A1 * | 1/2008 | Lodge | A61F 13/49 604/396 |
| 2010/0036340 A1 * | 2/2010 | Allison-Rogers | A61F 13/15699 604/367 |
| 2011/0184372 A1 * | 7/2011 | Esping Ostlin et al. | 604/392 |

FOREIGN PATENT DOCUMENTS

| | | |
|---|---|---|
| CN | 100406361 C | 7/2008 |
| EP | 0 122 042 A2 | 10/1984 |
| EP | 0 780 325 A1 | 6/1997 |
| GB | 2 264 278 A | 8/1993 |
| WO | WO 94/26222 A1 | 11/1994 |
| WO | WO 94/26224 A1 | 11/1994 |
| WO | WO 94/26225 A1 | 11/1994 |
| WO | WO 95/21107 A1 | 8/1995 |
| WO | WO 99/21522 A1 | 5/1999 |
| WO | 2005/063596 A1 | 7/2005 |
| WO | 2005/063597 A1 | 7/2005 |
| WO | WO 2005/063596 A1 | 7/2005 |
| WO | WO 2005/063597 A1 | 7/2005 |
| WO | WO 2006/025769 A1 | 3/2006 |

OTHER PUBLICATIONS

Written Opinion (PCT/ISA/237) dated Oct. 15, 2012, by the Swedish Patent Office as the International Searching Authority for International Application No. PCT/SE2012/050739.
Notification of Reexamination issued by the Chinese Patent Office in corresponding Chinese Patent Application No. 201110213021.8 dated May 31, 2017 (11 pages including partial English translation).
Office Action (Examination Decision on Reexamination) dated May 31, 2017, by the Chinese Patent Office in corresponding Chinese Patent Application No. 201110213021.8, and an English Translation of the Office Action. (13 pages).
Office Action dated Jun. 5, 2017, by the Mexican Patent Office in corresponding Mexican Patent Application No. MX/a/2014/000398. (5 pages).
Office Action dated Jan. 17, 2018, by the Mexican Patent Office in corresponding Mexican Patent Application No. 2014-000398, and an English Translation of the Office Action. (8 pages).
Notification of the First Office Action dated Oct. 15, 2018, by the State Intellectual Property Office of the People's Republic of China in corresponding Chinese Patent Application No. 201710761332.5 and an English translation of the Office Action. (13 pages).
Communication pursuant to Article 94(3) EPC dated Dec. 6, 2018, by the European Patent Office in corresponding European Patent Application No. 12 814 542.2. (5 pages).

\* cited by examiner

PACK MODULE COMPRISING ABSORBENT ARTICLES AND AT LEAST ONE BELT FUNCTIONING AS GRIPPING DEVICE

TECHNICAL FIELD

The present disclosure relates to a pack module of a number of absorbent articles, in particular to a pack module comprising a number of absorbent articles and at least one belt to which the absorbent articles can be releasably attached wherein the belt forms a gripping device when placed in the pack module.

TECHNICAL BACKGROUND

Within the field of absorbent articles, considerable efforts have been made for many years to permit an increase in the quantity of manufactured articles, for example baby articles or incontinence pads, per unit of volume, which is of great importance in connection with warehousing and transport. For example, twice as many baby articles are transported per lorry today compared with the number transported on a lorry of similar size several years ago.

On one hand, the above efforts involve providing thinner articles with an unimpaired high absorption capacity. Greater thinness has been achieved essentially by the introduction of gelling, so-called superabsorbents in an increasingly high concentration into the absorption bodies of the absorbent articles. This has resulted in improvements with regard to both storage and transport handling of the articles. Thinner absorbent articles have also been met with a positive response from their users, which has naturally also influenced various manufacturers to aim at developments in this direction.

On the other hand, the above efforts involve compressing the articles to a significantly greater degree than previously. Documents EP 0,122,042, GB 2,264,278 A, EP 0,780,325, WO2005/063597 and WO2005/063596 all relates to this compressing step.

A feature common to all packs that comprise firmly compressed absorbent articles is the difficulty in removing the first articles from the pack module. The article, in particular the first article, to be removed from the pack is in contact with (an) adjacent article/articles under high pressure and has surfaces which often exhibit relatively high friction with adjacent articles, as a consequence of which the force required to remove the first articles is high. Moreover, the fact that it is difficult to grip the firmly compressed articles when they are to be withdrawn from the pack also makes the removal of articles from the pack more difficult.

U.S. Pat. No. 4,934,535, WO 95/21107 and U.S. Pat. No. 5,377,837 disclose some methods for removing one article from a stack of articles by providing an opening on the top of the pack containing the stack so that the top part of the firmly compressed stack of absorbent articles extends beyond the top edge of the pack after the pack has been opened. The result is that the top part of the articles included in the stack is permitted to expand like a fan. However it is difficult to control all the remaining articles in the pack.

WO2006/025769A1 relates to an arrangement for removing an absorbent article from a stack of absorbent articles, wherein the arrangement comprises a gripping device provided in the form of a separate strip of material. One or two articles are drawn out first by friction between the strip and the article. In another embodiment, the strip is attached to the surface of the article.

In this arrangement, the gripping device is an additional strip and made by special materials to exhibit desired friction force for removing the article. The strip should be discarded after the article is drawn out.

There are disadvantages in the arrangement of WO 2006/025769. An additional strip increases the amount of material needed and increases the cost of the articles. In addition, the gripping device constitutes a piece of garbage after use which provides a negative environmental impact. In one of its embodiments, the attachment of the strip to the article is permanent by means of an adhesive, which makes separation of the article and the strip difficult. Another problem is that it is difficult to locate the components needed for attaching the first article on the wearer i.e. to find the belt. It is difficult to locate one single belt located somewhere in a bag together with a large number of absorbent articles.

Therefore, there is still a need for an arrangement for removing a firmly compressed absorbent article from a pack of articles.

SUMMARY

In view of the above disadvantages, an object of the present disclosure is to provide an arrangement for removing a firmly compressed absorbent article from a stack of articles without using any additional materials in order to save material and cost and reduce environmental impact.

Another object is to provide an arrangement that makes it easy to find the belt among a plurality of absorbent articles.

There are many kinds of belted-articles, such as belted-diapers disclosed in WO 99/21522, WO94/26224, WO94/26222, WO94/26225 and U.S. Pat. No. 4,964,960, which have separate belts to be placed around the waist of the wearer. However, WO2006/025769 does neither mention the possibility of substituting the strip of material with a belt nor the possibility of using a hook and loop connection between the strip and the article.

In the pack module according to the present disclosure, the belt of the belted-article is used as a gripping device. Thus, the belt substitutes the strip of the arrangement disclosed in WO 2006/025769. According to the present disclosure, a pack module is filled with beltless absorbent articles and at least one separate belt. One surface of the belt is in contact with the surface of at least one absorbent article to be removed from the pack module. One end of the belt is inserted between adjacent articles and the other end extends beyond a surface of the pack module, so that it can be gripped by a user to draw out the article.

To achieve said object, the present disclosure provides a pack module comprising a number of absorbent articles and at least one belt to which the absorbent articles can be releasably attached, wherein the belt when placed in the pack module constitutes a gripping device which is intended to act on at least one of the articles and, at least partially, remove at least one absorbent article from the pack module when the belt constituting the gripping device is used (i.e. when the user grips and pulls the gripping device).

In particular, the belt constituting the gripping device extends beyond at least one of the boundary surfaces of the pack module. In principle, it is enough that one end of the belt is arranged between adjacent articles in the pile and the rest of the belt sticks out of the pile on the opening side of the bag.

According to the present disclosure, the pack module is arranged in a pack comprising an opening and the belt constituting the gripping device is arranged at the boundary surface of the pack module which faces towards the opening of the pack so that the belt constituting the gripping device can be gripped by the user.

In particular, the belt constituting the gripping device comprises a gripping loop.

More specifically, the belt constituting the gripping device comprises a first surface and a second surface, with the first surface of the belt constituting the gripping device being in contact with the absorbent article on which the belt constituting the gripping device is intended to act, with the action occurring through friction between the first surface and the absorbent article.

Alternatively, the belt constituting the gripping device is intended to act on two absorbent articles, with the first surface of the belt constituting the gripping device being intended to act on one of the said two absorbent articles and with the second surface of the belt constituting the gripping device being intended to act on the other of the said two absorbent articles.

In an alternative embodiment, the belt constituting the gripping device is releasably attached to the backsheet of the absorbent article on which the belt constituting the gripping device is intended to act on.

Especially, the belt constituting the gripping device comprises at least one hook area and the at least one hook area is releasably attached to the absorbent article that is going to be at least partly removed from the pile of articles.

Alternatively, the belt comprises at least one adhesive area and the at least one adhesive area is releasably attached to the absorbent article that is going to be at least partly removed from the pile of articles.

In a specific embodiment, the belt constituting the gripping device constitutes an information carrier, with the information being able to for instance consist of text, images and/or symbols.

Especially, the information is a usage instruction for the belt and the absorbent articles.

To form the belt constituting the gripping device, the belt is folded at least once in longitudinal direction, while keeping the width of the belt, to make the belt constituting the gripping device shorter and easier to be handled.

Especially, the belt is folded a number of times so that the folded length is 10-30 cm, in particular 10-20 cm, such as 10-15 cm.

In particular, the belt is folded in a manner so that the at least one hook area is provided on the outwardly oriented surface when the belt is folded. Said at least one hook area is then placed between articles in the pile and due to the textile backsheet of the absorbent articles the hook area will attach to at least one article.

With the arrangement of the present disclosure, the beltless absorbent articles and at least one separate belt are filled in a pack module. One surface of the belt is in contact with the surface of at least one absorbent article to be removed from the pack module. One end of the belt is inserted between adjacent articles or between one article and the wall of the pack module, while the other end extends beyond a surface of the pack module, so that it can be gripped by a user. The belt is intended to act on at least one of the absorbent articles and to, at least partially, remove at least one absorbent article from the pack module when the belt is pulled out of the pack module. The action may occur through friction between the belt and the surface of the absorbent article. The action may also occur through a hook and loop attachment. Hooks on the belt may cooperate with a textile-like backsheet on the absorbent article. After the belt and the article are removed, the belt is placed around the waist of a wearer. Then the absorbent article is releasably attached to the belt. The belt can be reused for attaching a new article removed from the pack. While not discarding the belt, saves material and cost of the article.

In the arrangement of WO 2006/025769, the strip will be discarded after it has been used. It shall be noted that it therefore is made as small as possible but still so long that it can draw the article from the pack. The friction may be improved by using different materials with higher friction.

In the present disclosure, the belt provides a larger contact area with the article to be removed, which means that more friction is provided without the need of any special high friction material. In the embodiment where the belt is folded so that a hook area on the belt is oriented outwardly to cooperate with an outwardly oriented nonwoven surface of the absorbent article intended to be removed, the function of the belt utilized as a gripping device is even further improved due to the hook & loop connection between the gripping device/belt and the absorbent article.

Another advantage of the present disclosure is that there is no need for a separate gripping device with the only purpose of removing an article from the pack, in other words, the belt also can be utilized as a gripping device to remove firmly compressed articles from a pack module before it is utilized as a belt.

Double use of a material or a component, as in the present disclosure, means less material cost for the producer which make the article cheaper for the consumer. It also means less material to dispose which reduces the burden on the environment. The use of less material also means less transportation of material which also reduces negative environmental impact.

A further advantage with the present disclosure is that the person removing the first absorbent article by pulling the belt catches both the absorbent article and the belt at the same time, i.e. both components necessary for applying the article on the wearer. This saves times for the person (e.g. a nurse or the wearer himself/herself) which is to apply the article on the wearer.

BRIEF DESCRIPTION OF THE DRAWINGS

The present disclosure will now be explained in more detail with reference to certain non-limiting embodiments and with reference to the accompanying drawings, in which:

FIG. 7a-7c shows how to fold the belt with the hook element oriented outside.

DETAILED DESCRIPTION

Embodiments of the present disclosure will be described below with reference to the drawings.

The term "absorbent article" or "article" is to be understood as meaning an article selected from the group consisting of diapers, male or female incontinence guards, belt-diapers, etc. Such articles are used for the absorption of bodily exudates, such as blood, urine, sweat and faeces.

The term "gripping device" in the detailed description of specific embodiments is to be understood as "belt constituting the gripping device".

Figure 1:
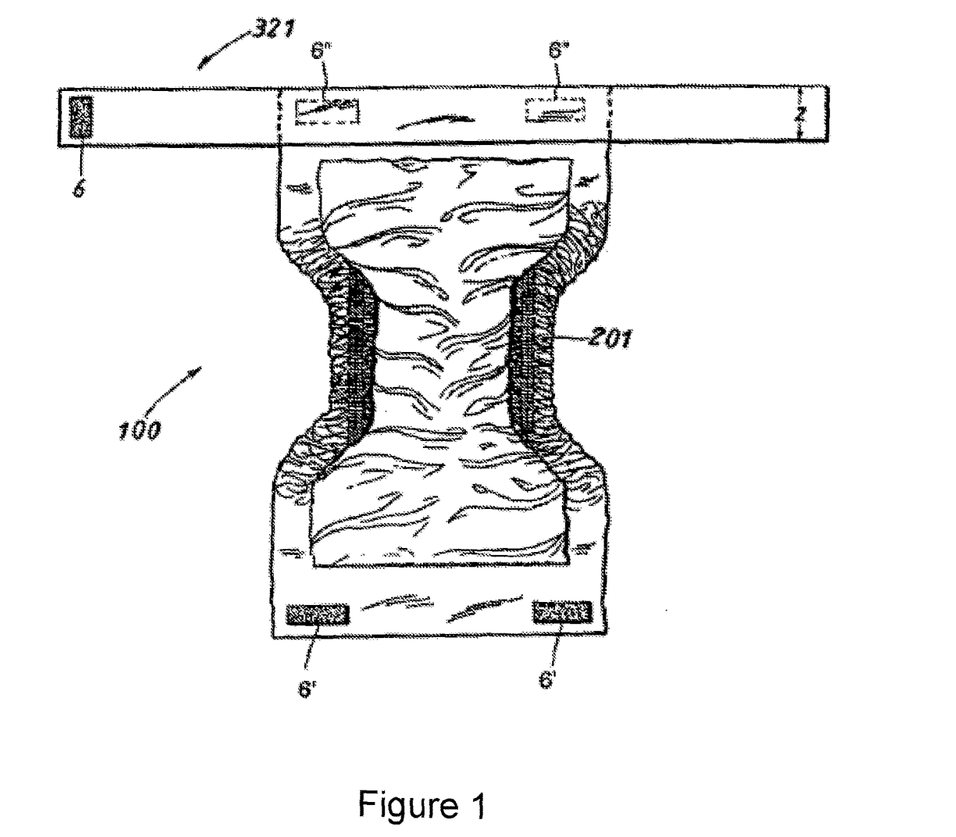
FIG. 1 is a plan view showing an absorbent assembly with an absorbent article and a separate belt.

FIG. 1 is an absorbent assembly 100 consisting of an absorbent article 201 and a separate belt 321 to which the article 201 is releasably attached. One end of the belt 321 is provided with an attaching element 6 (second attachment) to be attached to the other end of the belt 321. The attaching element 6 may be a hook element or an adhesive strip 6 to be attached to a loop element or a landing zone on the other end of the belt 321. In addition, an attachment (first attachment) between the belt and the article may be in the form of a hook & loop connection with hook elements provided on the article and loop elements provided on the belt 321. The hook & loop connection between the belt and the article is known in the art and further description thereto is therefore omitted.

The belt 321 may have more than one attaching element 6 on one of its end.

The absorbent article 201 shown in FIG. 1 comprises a liquid-permeable topsheet, a liquid-impermeable backsheet and an absorbent core located there between.

The topsheet of the absorbent article is the layer which lies in contact with the wearer's body when the article is in use. As such, it should be soft, non-irritating and comfortable against the skin, and bodily fluid should be able to pass through it without hindrance.

The absorbent core of the absorbent article acts to receive and contain liquid and other bodily exudates. As such, it typically comprises absorbent material.

The backsheet of the absorbent article is the layer which lies furthest from the wearer's body when the article is in use. To protect the wearer's garments from soiling, it should be liquid-impermeable, but is desirably gas-permeable (i.e. breathable) to allow air and vapour to pass in and out of the article so that the warm, damp conditions which can arise in the article are reduced. Typically, the backsheet is of a liquid-impervious material, such as a thin plastic film, e g a polyethylene or polypropylene film, a nonwoven material coated with a liquid-impervious material, a hydrophobic nonwoven material which resists liquid penetration or a laminate comprising plastic film(s) and nonwoven material(s). Examples of breathable backsheet materials are porous polymeric films, nonwoven laminates from spunbond and meltblown layers, laminates from porous polymeric film(s) and nonwovens.

For the package and transport of the articles in compact volume, the articles 201 should be folded at first. Generally, the articles 201 are folded in a manner so as to direct the backsheet towards the outside in order to prevent the article, especially the topsheet, from being polluted. Then the folded articles 201 are packed under compression into a pack module. The separate belt 321 will be used as a gripping device 320 in accordance with the present disclosure. The article can be removed via friction between the belt 321 and the backsheet of the article, releasable attachment between the hook element 6 on belt 321 and the textile-like backsheet of the article 201, or the releasable attachment between the adhesive strip 6 on the belt 321 and the backsheet (made of plastic film) of the article 201. The embodiments of the belt constituting the gripping device 320 will be described in detailed with reference to FIGS. 3a-3c and FIG. 6.

Figure 2:
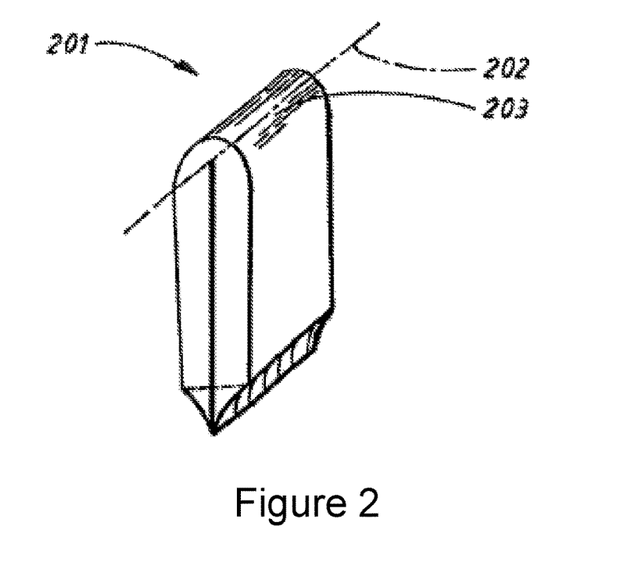
FIG. 2 is a schematic representation of the absorbent article that is folded when the absorbent article is packed.

FIG. 2 is a schematic representation of an absorbent article 201 that is folded in a way which is commonly encountered when the absorbent article 201 is packed.

The article 201 is folded along an essentially transverse fold line 202, essentially in the middle of the article 201 in its longitudinal direction. The area adjacent to the fold line 202 constitutes the fold area 203 of the article 201. The method of folding articles 201 along only one essentially transverse fold line 202 is particularly common for smaller articles 201, such as baby articles.

Alternative folding procedures are also encountered. It can be mentioned by way of example that larger absorbent articles, such as incontinence pads for adult incontinent users or larger baby articles, are often folded along two essentially transverse fold lines. In this case, one of the essentially transverse fold lines is arranged in the front half of the incontinence pad, and the other fold line in the rear half of the incontinence pad, which transverse fold lines divide the incontinence pad into three parts of essentially identical length in the longitudinal direction of the incontinence pad. An incontinence pad or article folded along two essentially transverse fold lines thus exhibits two fold areas, one adjacent to each fold line. An incontinence pad or an article that has been folded along two fold lines exhibits a smaller surface area in its folded state, so that a pack containing the folded incontinence pads can be made easier to handle.

As an alternative, it is also possible to consider folding the article along an additional one or more fold lines.

Figure 3A:
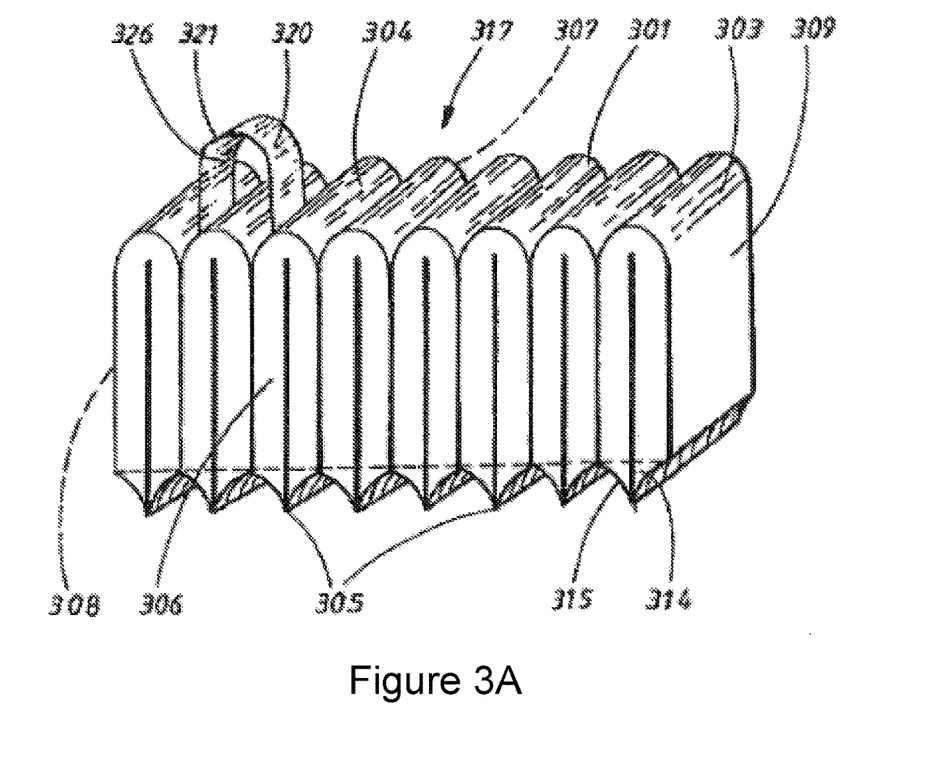
FIG. 3a is a schematic view of a pack module comprising an arrangement for the removal of an article from a pack module in accordance with one embodiment.

FIG. 3a illustrates how absorbent articles 301, folded in accordance with FIG. 2, are configured in a pack module 317 in accordance with a first embodiment. The pack module 317 comprises eight articles 301, although it can naturally contain more or fewer articles 301. The pack module 317 exhibits essentially rectangular parallelepipedic form comprising six outward-facing boundary surfaces. All the articles 301 in the pack module 317 are oriented in the same way in the pack module 317, so that the fold areas 303 of all the articles 301 are arranged at the same boundary surface 304 in the pack module 317. The front and rear transverse edges 314, 315 of the articles 301 are arranged at the opposite boundary surface 305 of the pack module 317. The pack module 317 also includes a front boundary surface 306 and a rear boundary surface 307, which boundary surfaces 306, 307 are essentially perpendicular to the boundary surfaces 304, 305. The pack module 317 also includes a first end surface 308 and a second end surface 309, in which case these also constitute boundary surfaces for the pack module 317.

The pack module 317 comprises at least one gripping device 320. The gripping device 320 is formed by the belt 321 folded to a desired length and is intended primarily to facilitate the removal of an article from a pack module 317, for which purpose the gripping device 320 is in the form of gripping flap or gripping loop which projects beyond one of the boundary surfaces of the pack module 317. It is possible to remove at least one article 301, at least partially, from the pack module 317 by actuating the gripping device 320 by pulling it. The use of a gripping device 320 is particularly advantageous when the first article 301 is to be removed from a firmly compressed pack module 317. After removing the first article 301, the compression of the articles 301 in the pack module 317 is reduced. However, if one pack module 317 is assigned with more than one belt 321, it is possible for the pack modules 317 to contain more than one gripping devices 320. The gripping device 320 illustrated in FIG. 3a is intended to act on article 301 number two from the left in the pack module 317. The gripping device 320 can naturally be intended to act on any article in pack module 317. The gripping device 320 is connected to the article 301 that is intended to be removed as the first of all the articles 301 from the pack module 317, that is to say the article 301 to be removed when the pack module 317 is compressed to its maximum extent and when the pressure from adjacent articles 301 in the pack module 317 is at its greatest.

The function of the gripping device 320, in accordance with the first embodiment, is dependent on friction between the gripping device 320 and the outward-facing surface of the folded article 301, and on the fact that surrounding articles 301 press the gripping device 320 against the article 301 to which the gripping device is attached. If the gripping device 320 is attached to one of the outermost articles 301 in the pack module 317, the function of the gripping device 320 will depend on the pressure from the nearest article 301 and the end pressure from the packing wrapper in which the pack module 317 is packed.

The gripping device 320 is arranged in such a way in relation to the article 301 that a gripping loop 326 is created between the gripping device 320 and the fold area 303 of the article 301, in which case at least one finger can be introduced into the gripping loop 326 when the article 301 is to be removed from the pack module 317.

The distance by which the article 301 can be removed from other articles 301 in the pack 317 with the help of the gripping device 320 will differ depending on the distance by which the gripping device 320 extends into the pack module 317 from the boundary surface 304 of the pack module 317 towards the opposite boundary surface 305 of the pack module 317.

If the gripping device 320 extends into the pack module 317 for only a short distance, the pressure of the surrounding articles 301 against the gripping device 320 will be released after only a short distance, in which case the frictional forces between the gripping device 320 and the article 301 to be removed from the pack module 317 will also cease. It is usually sufficient, however, for the article 301 to be removed from the pack module 317 with the help of the gripping device 320 to an extent sufficient to permit the individual article 301 to be gripped firmly in order to finally remove it from the pack module 317. If, on the other hand, the gripping device 320 extends as far as to the boundary surface 305, pressure from surrounding articles 301 against the gripping device 320 and the article 301 that the gripping device 320 is intended to act on will be retained until the article has been removed in its entirety from the pack module 317.

The gripping device 320 extends beyond the boundary surface 304 of the pack module 317, so that it is easy to find where the gripping device is located.

It is possible in alternative embodiments for more than one gripping device 320 to be present when one pack module 317 is assigned with more than one belt 321, and for each gripping device to be attached to a specific article 301 in the pack module 317.

It is also possible to consider the attachment of the gripping device 320 to two articles 301, in which case both articles 301 are removed from the pack module 317 when the gripping device 320 is used.

It is also possible to consider the arrangement of the gripping device 320 in such a way as to act on three or more adjacent articles 301 in the pack module 317, in which case the gripping device 320 is attached to the articles 301 on which the gripping device 320 is intended to act which are arranged furthest apart. The articles 301 arranged between the two articles 301 arranged furthest apart are then acted on indirectly when the gripping device 320 is used.

Figure 3B:
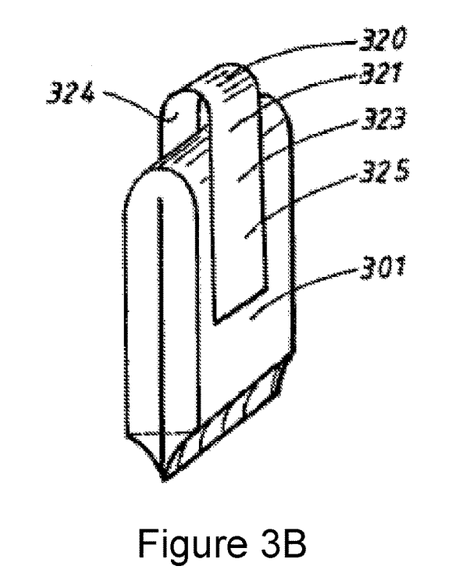
FIG. 3b is a schematic view of an article contained in the pack module in FIG. 3a, which article comprises the arrangement for removing the article from the pack module.

The specific article 301 in the pack module 317 to which the gripping device 320 is attached, that is to say article 301 number two from the left in the pack module 317 in FIG. 3a, is illustrated in FIG. 3b. The gripping device 320 is formed by the belt 321, which belt 321 consists of a laminate 323. The laminate 323 constituting the belt 321 exhibits a carded loop nonwoven on one of its outermost surfaces and a spun bond nonwoven on its other outermost surface. The carded loop nonwoven does exhibit a slightly higher coefficient of friction than the spun bond nonwoven. Due to this difference in coefficient of friction it is advantageous to arrange the belt constituting the gripping device with its loop surface against the article 301 to be removed. The article to be removed exhibits a higher friction to the gripping device than the surrounding articles in the pack module 317.

In an alternative embodiment, alternative materials for the gripping device 320 may exhibit the same frictional characteristics on both sides, anyhow the gripping device 320 can draw out the article from the pack because the gripping device 320 is in contact with both sides of the article 301 that is intended to be acted on by the gripping device 320 while it is in contact with only one side of the immediately adjacent articles 301. The result is that the force transferred to the article that is to be removed by means of the gripping device is twice as great as the force transferred to adjacent articles 301. It has also emerged that it is easy for a user to push against the adjacent articles 301 with the fingers of one hand when pulling one article 301 from the pack module 317 with the help of the gripping device 320.

Figure 3C:
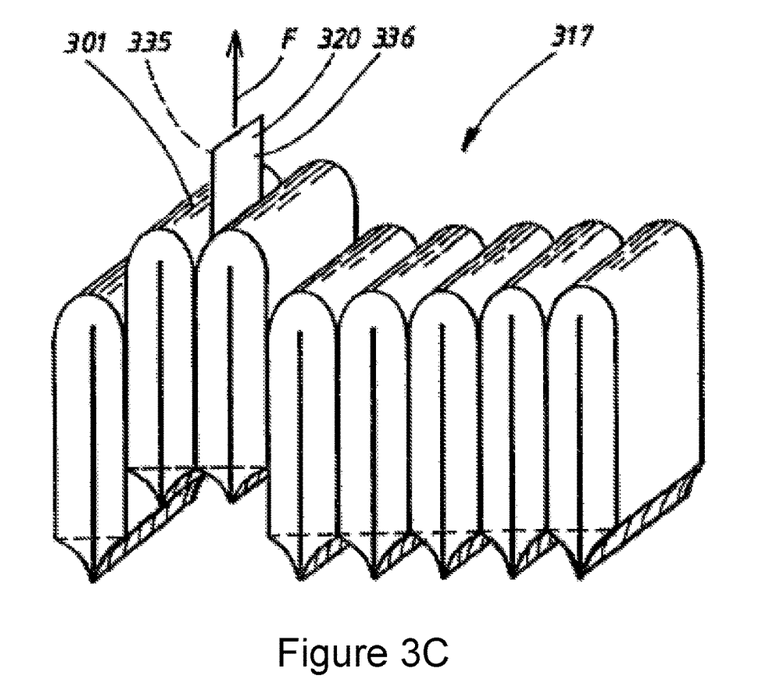
FIG. 3c shows an alternative embodiment of a pack module comprising a belt constituting the gripping device arranged to act on two articles.

Illustrated in FIG. 3c is an alternative aspect of a pack module 317 comprising a gripping device 320 intended to act on two articles 301, in which the first surface 335 of the gripping device 320 acts on the article 301 that is in contact with the said first surface 335, and the second surface 336 of the gripping device 320 acts on the article 301 that is in contact with the said second surface 336. The gripping device 320 is formed by the belt 321 which is arranged between two articles 301 in the pack module 317, in which case the function of the gripping device 320 is dependent on friction between the gripping device 320 and the two articles 301 between which the gripping device 320 is arranged. The gripping device is executed so that the coefficient of friction between both surfaces of the gripping device 320 and the surfaces of the adjacent articles 301 is greater than the coefficient of friction between two articles 301. In order to achieve a satisfactory function, the difference in the coefficient of friction should be at least 0.1.

When the gripping device 320 is subjected to a tensile force F, the immediately adjacent article 301 to either side of the gripping device 320 accompanies the latter from the pack module 317. FIG. 3c shows the pack module 317 after the gripping device 320 has partially removed two articles 301 from the pack module 317. The distance for which the articles 301 accompany the gripping device 320 when it is used will differ depending on the extent to which the gripping device 320 projects between the articles 301 in the pack module 317. However, the gripping device 320 should project in between the articles 301 sufficiently to enable the articles 301 to be withdrawn from the pack module 317 with the help of the gripping device 320 for a distance which is sufficiently long to permit a secure grip to be effected directly around the two articles 301 after the gripping device 320 has ceased to function. Final removal of the two articles 301 from the pack module 317 can then be performed by gripping the two articles 301 and withdrawing them from the pack module 317. The reason why the articles 301 can be removed only partially from the pack module 317 if the gripping device 320 projects for only a short distance between the articles 301 is that the normal force against the surface of the gripping device 320 reduces/ceases when the compressive forces from surrounding articles 301 in the pack module 317 cease, in conjunction with which the frictional forces are also reduced/cease.

Figure 4:
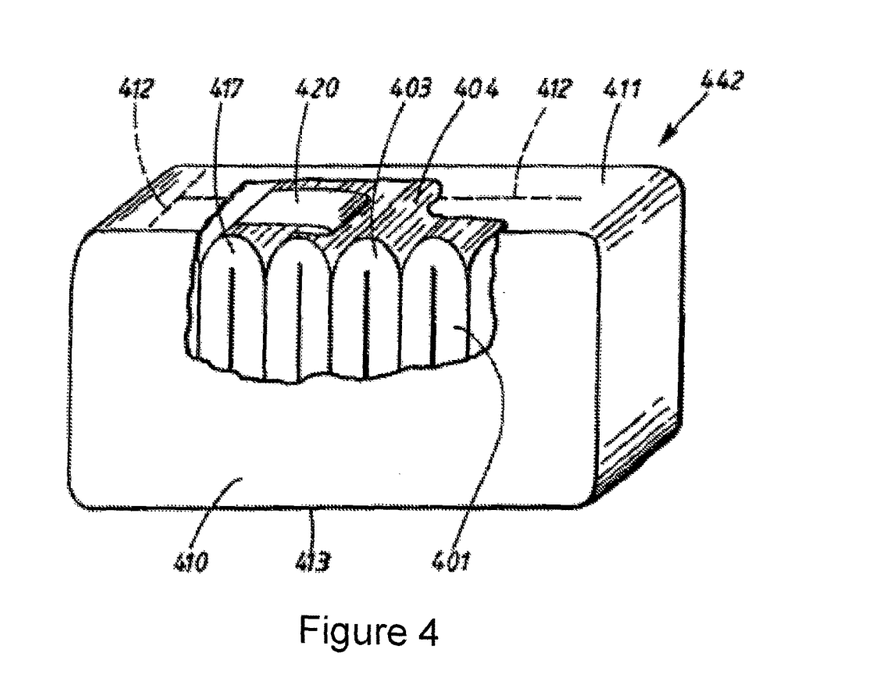
FIG. 4 shows an unopened pack comprising a pack module comprising an arrangement for removing an article from the pack.

Illustrated in FIG. 4 is a pack 442, into which a pack module 417 comprising a gripping device 420 functioning by means of friction is introduced. The pack module 417 is arranged in the same way as the pack module 317 in FIG. 3a. In order to illustrate more clearly how the pack module 417 is arranged inside the pack 442, a part of the front side 410 and the top side 411 of the pack has been removed in FIG. 4. The pack module 417 contains eight articles 401, but can naturally contain a larger or smaller quantity of articles 401. The pack 442 consists of a plastic bag, although in alternative embodiments it may consist of a paper bag or some other suitable material. It is also possible to consider a pack 442 consisting of a material combination comprising, for example, a laminate consisting of a plastic film and a paper layer, where the plastic film makes the pack 442 tight and the paper layer gives the pack 442 strength.

A pack module 417 can alternatively be enclosed in a sleeve, as described in patent specification WO 93/16925. The pack module 417 provided with a sleeve can then be enclosed in a bag made of a suitable material or supplied without any extra wrapping material. It is also possible to consider vacuum-packing one or more pack modules 417 in accordance with the present disclosure inside an essentially airtight plastic pack.

In alternative embodiments, the pack 442 can contain a number of pack modules 417 arranged side by side or one above the other. It is also possible to consider large packs 442 containing pack modules 417 arranged both side by side and in a number of layers one above the other.

The articles 401 in the pack module 417 can be arranged in an alternative fashion inside the pack 442; for example, the fold areas 403 of the articles 401 can face towards the bottom surface 413 of the bag or towards either the front side 410 of the bag or its opposite rear side.

The top side 411 of the pack 442 constitutes the opening side of the pack 442 and comprises a T-shaped perforation 412, which is capable of being broken open and is intended to be broken open when the pack 442 is to be opened.

The gripping device 420, which extends beyond the boundary surface 404 of the pack module 417, lies folded down onto the boundary surface 404 below the opening side of the pack 442.

Figure 5:
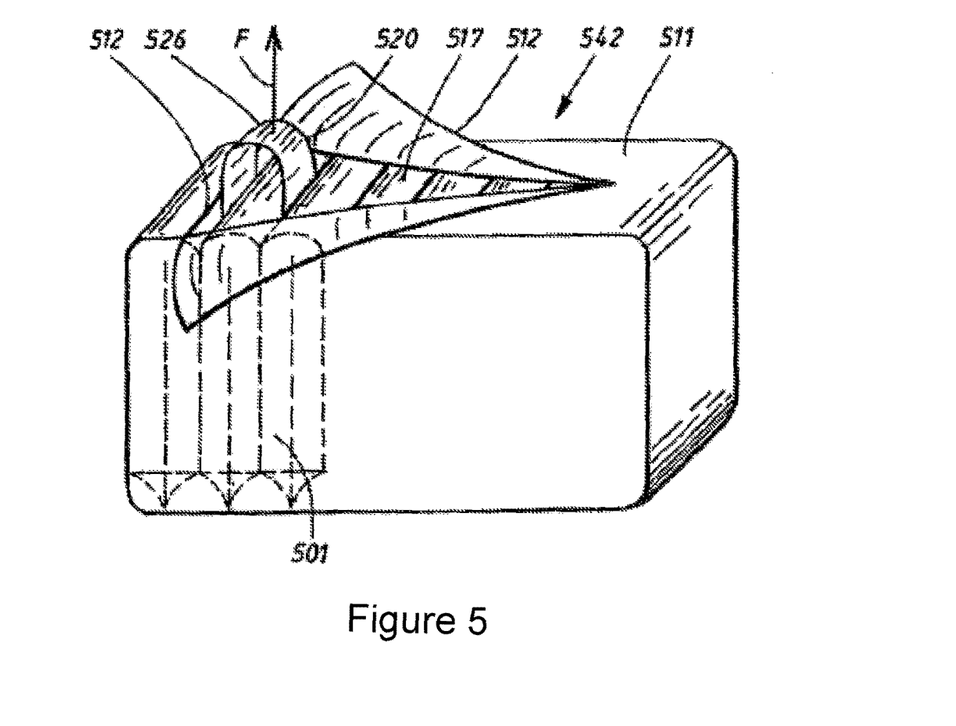
FIG. 5 shows the pack in accordance with FIG. 4 in the opened state.

Illustrated in FIG. 5 is a pack 542 in the opened state. The pack 542 is executed in the same way as the pack 442 in FIG. 4, but the T-shaped perforation 512 of the pack 542 is broken open. In conjunction with the breaking open of the perforation 512, the gripping device 520 has risen up from its folded-down position under the top side 511 of the pack 542. When the first article 501 is to be removed from the pack module 517 contained in the pack 542, a finger is expediently introduced through the gripping loop 526 that is formed between the article 501 to be removed from the pack 542 and the gripping device 520. The article 501 is then removed by the application of a tensile force F to the gripping loop 526.

Figure 6:
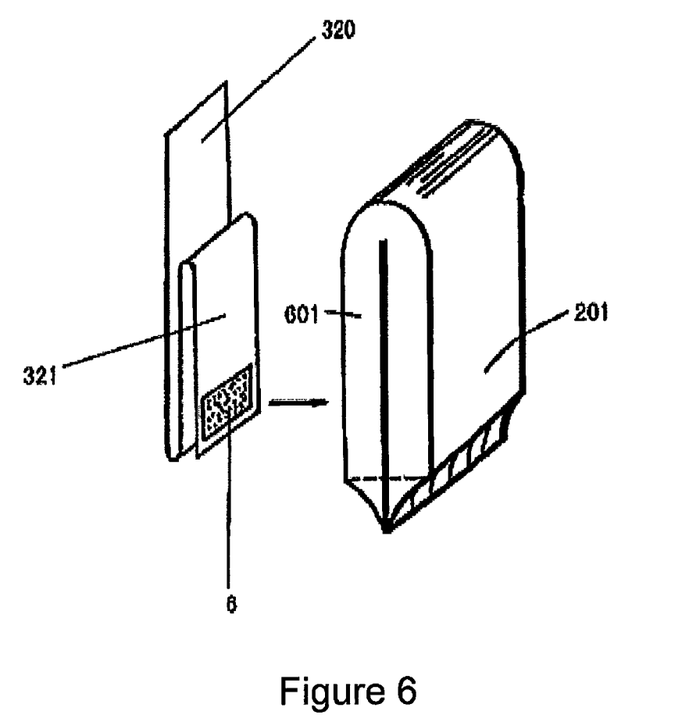
FIG. 6 shows an alternative embodiment of an arrangement for removing an article from the pack.

Illustrated in FIG. 6 is an alternative embodiment of an arrangement for the removal of an article from a pack module, which arrangement comprises a gripping device 320. The gripping device 320 is formed by the belt 321. The gripping device 320 is releasably attached to the backsheet of the article. In this case, the whole belt 321 can be released from the article before the article is put on the wearer.

The belt 321 is folded to have a desired length which is long enough to be inserted at one end between the articles or between the first one article and the wall of the pack and stick out the other end outside the boundary surface 304. As mentioned above, the belt 321 has at one end a hook element 6 (second attachment). The belt 321 is folded in a manner such that the hook element 6 (second attachment) is exposed on the outside of the folded belt. Then the gripping device 320 is completed. The gripping device 320 is inserted between adjacent articles or between one article and the wall of the pack with the hook element 6 facing the back sheet of the article 201. If the backsheet of the article 201 is of textile material, the hook element 6 (second attachment) of the gripping device 320 will be releasably attached to the back sheet to form a hook & loop connection. To remove the article, the gripping device 320 is pulled up so that the article attached to the gripping device 320 is removed from the pack by the engaging force between the hook element and the back sheet.

In this embodiment, the attachment can be separable, in which case the entire gripping device 320 can be released from the article 201 before the article 301 is put on a wearer. After separating the belt and the article, the belt can be used in a conventional manner with the article.

Alternatively, if the backsheet of the article 201 is formed of plastic film, the hook element 6 on the belt 321 can be replaced by an adhesive strip to be releasably attached to the backsheet of the article.

In the pack module according to the present disclosure, the belt 321 is generally a reusable belt. When one article 201 is used up, it is released from the belt and is discarded. Then another new article is removed from the pack and is attached to the belt again. The reusable belt saves materials and cost of the article.

FIG. 7a-7c is a schematic view showing one example of how a belt is folded. FIG. 7a shows the unfolded belt with a hook element 6 provided on one of its end. In FIG. 7b, the belt is folded once along the longitudinal length of the belt to make the hook element 6 facing outside (while keeping the width of the belt). Then the belt is folded twice along the longitudinal length of the belt to assume the shape shown in FIG. 7c in which the hook element 6 is still directed outside, i.e. exposed to be accessible to the article to be removed.

Of course, the belt may be folded in any other way as long as its final length is suitable to function as a gripping means as described above. In the specific embodiments, the belt is folded a number of times so that the folded length is 10-30 cm, such as 10-20 cm or 10-15 cm.

Regardless of whether the gripping device is intended to act on the article through frictional forces or through the attachment of the gripping device to the article to be acted on, the gripping device is suitable as a carrier of information between the manufacturer and the customer. The gripping device may in this case contain information in the form of text, images, symbols or a combination of at least two of these forms of information. The gripping device can include information about forthcoming new products, for example.

Although the embodiments of the present disclosure have been described above, the present disclosure is not limited to the above embodiments, but various changes and modification may be made therein within the scope of the technical concept described in the scope of the claims.

The invention claimed is:

1. A pack module comprising:
a plurality of absorbent articles; and
at least one belt including an attaching element at one end of the at least one belt,
wherein the at least one belt is configured to be releasably attached to any one of the plurality of absorbent articles,
wherein the at least one belt is configured to be attached around a waist of a user by wrapping the at least one belt around the waist of the user and touching another end of the at least one belt with the attaching element,
wherein the any one of the plurality of absorbent articles is wearable by the user by attaching the at least one belt around the waist of the user and attaching the any one of the plurality of absorbent articles to the belt, and
wherein the at least one belt is placed in the pack module as a gripping device that grips at least one of the absorbent articles, so that the at least one absorbent article is at least partially removable from the pack module when the gripping device is pulled.

2. A pack module according to claim 1, wherein the at least one belt constituting the gripping device extends beyond at least one boundary surface of the pack module.

3. A pack module according to claim 1, wherein the pack module is arranged in a pack comprising an opening, and the at least one belt constituting the gripping device is arranged at a boundary surface of the pack module which faces towards the opening of the pack.

4. A pack module according to claim 1, wherein the at least one belt constituting the gripping device comprises a gripping loop.

5. A pack module according to claim 1, wherein the at least one belt constituting the gripping device comprises a first surface and a second surface, with the first surface of the at least one belt constituting the gripping device being in contact with the at least one absorbent article which the gripping device is configured to act on, with the action occurring through friction between the first surface and the at least one absorbent article.

6. A pack module according to claim 1, wherein the at least one belt constituting the gripping device is configured to act on two absorbent articles, with a first surface of the at least one belt constituting the gripping device being configured to act on one of the two absorbent articles and with a first second surface of the at least one belt constituting the gripping device being intended to act on the other of the two absorbent articles.

7. A pack module according to claim 1, wherein the at least one belt constituting the gripping device is releasably attached to a back sheet of the at least one absorbent article on which the gripping device is configured to act.

8. A pack module according to claim 7, wherein the at least one belt constituting the gripping device comprises at least one hook area and the at least one hook area is releasably attached to the at least one absorbent article that is to be at least partly removed from the pack module.

9. A pack module according to claim 7, wherein the at least one belt constituting the gripping device comprises at least one adhesive area and the at least one adhesive area is releasably attached to the at least one absorbent article that is to be at least partly removed from the pack module.

10. A pack module according to claim 1, wherein the at least one belt constituting the gripping device is folded at least once in a longitudinal direction, with a width of the at least one belt being kept constant, to make the at least one belt constituting the gripping device shorter than when the at least one belt is not folded.

11. A pack module according to claim 1, wherein the at least one belt is folded a number of times so that the folded length is within the range of 10-30 cm.

12. A pack module according to claim 11, wherein the at least one belt is folded a number of times so that the folded length is within the range of 10-20 cm.

13. A pack module according to claim 12, wherein the at least one belt is folded a number of times so that the folded length is within the range of 10-15 cm.

14. A pack module according to claim 8, wherein the at least one belt is folded in a manner so that the at least one hook area is oriented on an outwardly oriented surface when the at least one belt is folded.

15. A pack module according to claim 1, wherein the at least one belt includes first and second attachments, the first attachment is configured to be releasably attached to the any one of the plurality of absorbent articles such that the any one of the plurality of absorbent articles is wearable by a user and attachable by the at least one belt around a waist of the user, and the second attachment is configured to act on the at least one of the absorbent articles, and to at least partially remove the at least one absorbent article from the pack module when the gripping device is used, wherein the second attachment includes the attaching element.

* * * * *